(12) United States Patent
Maitra et al.

(10) Patent No.: US 10,214,502 B2
(45) Date of Patent: Feb. 26, 2019

(54) METHOD OF INHIBITING APOLIPOPROTEIN-E EXPRESSION WHILE INCREASING EXPRESSION OF AT LEAST ONE OF LDL-RECEPTOR PROTEIN OR ABCA1 PROTEIN COMPRISING ADMINISTERING A SMALL COMPOUND

(71) Applicants: California State University, Fresno, Fresno, CA (US); Mayo Foundation for Medical Education and Research, Rochester, MN (US)

(72) Inventors: Santanu Maitra, Clovis, CA (US); Jungsu Kim, Ponte Vedra, FL (US)

(73) Assignees: Mayo Foundation for Medical Education and Research, Rochester, MN (US); California State University, Fresno, Fresno, CA (US)

( * ) Notice: Subject to any disclaimer, the term of this patent is extended or adjusted under 35 U.S.C. 154(b) by 0 days.

(21) Appl. No.: 15/285,296

(22) Filed: Oct. 4, 2016

(65) Prior Publication Data

US 2018/0093960 A1  Apr. 5, 2018

(51) Int. Cl.
*C07D 295/26* (2006.01)
*C07C 233/65* (2006.01)
(Continued)

(52) U.S. Cl.
CPC ......... *C07D 295/26* (2013.01); *A61K 31/137* (2013.01); *A61K 31/166* (2013.01); *A61K 31/167* (2013.01); *A61K 31/18* (2013.01); *A61K 31/40* (2013.01); *A61K 31/4453* (2013.01); *A61K 31/5375* (2013.01); *C07C 211/30* (2013.01); *C07C 233/64* (2013.01); *C07C 233/65* (2013.01); *C07C 233/75* (2013.01); *C07C 311/16* (2013.01); *C07C 311/20* (2013.01); *C07C 311/21* (2013.01);
(Continued)

(58) Field of Classification Search
CPC .. A61K 31/137; A61K 31/166; A61K 31/167; A61K 31/18; A61K 31/40; A61K 31/4453; A61K 31/5375
USPC ...................................... 514/237.5
See application file for complete search history.

(56) References Cited

U.S. PATENT DOCUMENTS 8,193,389 B2  6/2012  Neitzel et al.
8,604,055 B2 * 12/2013  Baruah ............... C07D 213/73
                                                  514/235.2
(Continued)

OTHER PUBLICATIONS

Basak, Jacob et al. (AN 2012:1801878) HCAPLUS, DN 158:676519, abstract of Molecular Neurodegeneration (2012), 7, 14).*
(Continued)

*Primary Examiner* — Sabiha N Qazi
(74) *Attorney, Agent, or Firm* — Fish & Richardson P.C.

(57) ABSTRACT

This invention offers an effective method of decreasing expression of apolipoprotein E and increasing expression of at least one of either LDL-receptor protein or AbcA1 protein including selecting mammalian cells expressing apoE and at least one of either LDL-receptor protein or AbcA1 protein, contacting the mammalian cell with an effective amount of a compound having general formula (I) or general formula (II) in an amount sufficient to decrease expression of the apoE and increase expression of at least one of the LDL-receptor protein or the AbcA1 protein in the mammalian cell.

6 Claims, 6 Drawing Sheets

(51) Int. Cl.
| | |
|---|---|
| C07D 295/195 | (2006.01) |
| C07C 311/16 | (2006.01) |
| C07D 295/03 | (2006.01) |
| C07C 211/30 | (2006.01) |
| A61K 31/166 | (2006.01) |
| A61K 31/5375 | (2006.01) |
| A61K 31/40 | (2006.01) |
| A61K 31/4453 | (2006.01) |
| A61K 31/18 | (2006.01) |
| A61K 31/137 | (2006.01) |
| A61K 31/167 | (2006.01) |
| C07C 233/75 | (2006.01) |
| C07C 233/64 | (2006.01) |
| C07C 311/21 | (2006.01) |
| C07C 311/20 | (2006.01) |

(52) U.S. Cl.
CPC ....... *C07D 295/03* (2013.01); *C07D 295/195* (2013.01); *C07C 2101/14* (2013.01)

(56) References Cited

U.S. PATENT DOCUMENTS

| | | | | | |
|---|---|---|---|---|---|
| 8,633,195 | B1 * | 1/2014 | Maitra | ............... | A61K 31/135 |
| | | | | | 514/252.12 |
| 8,871,507 | B2 * | 10/2014 | Maitra | ............... | A61K 31/135 |
| | | | | | 435/366 |
| 8,897,507 | B2 * | 11/2014 | Suzuki | ............... | G06K 9/00248 |
| | | | | | 382/118 |
| 9,765,030 | B2 * | 9/2017 | Baruah | ............... | C07D 215/14 |
| 9,782,407 | B2 * | 10/2017 | Baruah | ............... | C07D 213/73 |

OTHER PUBLICATIONS

"2012 Alzheimer's disease facts and figures." Alzheimer's & Dementia 8 (2012) 131-168.
Bales, K.R., et al. (1999),"Apolipoprotein E is essential for amyloid deposition in the APPV717F transgenic mouse model of Alzheimer's disease." PNAS 96(26) 15233-15238.
Bateman, RJ, et al. (2011). "Autosomal-dominant Alzheimer's disease: a review and proposal for the prevention of Alzheimer's disease." Alzheimer's Research 8, Therapy 3:1-13.
Bien-Ly, Nga, et al. (2012). "Reducing Human Apolipoprotein E Levels Attenuates Age-Dependent Aβ Accumulation in Mutant Human Amyloid Precursor Protein Transgenic Mice." J Neurosci. 32(14): 4803-4811.
Michael S. Brown and Joseph L. Goldstein (1985). "A Receptor-Mediated Pathway for Cholesterol Homeostatis." Physiology or Medicine. 284-324.
Castellano, J.M., et al. (2011). "Human apoE isoforms differentially regulate brain amyloid-β peptide clearance." Sci Transl Med. 3(89): 1-21.
Corder, EH, et al. (1993), "Gene Dose of Apolipoprotein E Type 4 Allele and the Risk of Alzheimer's Disease in Late Onset Families." Science 261(5123): 921-923.
Dergunov, A.D. (2006). "Role of ApoE in Conformation Prone Diseases and Atherosclerosis." Biochemistry (Moscow), 71(7):707-712.
Fullerton, S.M., et al. (2001). "Impairment of the Blood-Nerve and Blood-Brain Barriers in Apolipoprotein E Knockout Mice." Exp Neurol 169:13-22.

Hebert, L.E., et al. (2003), "Alzheimer Disease in the US Population Prevalence Estimates Using the 2000 Census," Arch Neurol 60:1119-1122.
Ji, G., et al. (2003). "Apolipoprotein E Isoform-Specific Regulation of Dendritic Spine Morphology in Apolipoprotein E Transgenic Mice and Alzheimer's Disease Patients." Neuroscience 122: 305-315.
Kim, J., et al. (2009). "Overexpression of Low-Density Lipoprotein Receptor in the Brain Markedly Inhibits Amyloid Deposition and Increases Extracellular Ab Clearance." Neuron 64:632-644.
Kim, J., et al. (2011). "Haploinsufficiency of Human APOE Reduces Amyloid Deposition in a Mouse Model of Arnyloid-Amyloidosis." J. Neurosci, 31(49):18007-18012.
Koldamova, R., et al. (2014). "ATP-Binding Cassette Transporter A1: from metabolism to neurodegeneration." Neurobiol Dis. 72PA: 13-21.
Liao, F., et al. (2014). "Anti-ApoE Antibody Given after Plaque Onset Decreases A-Beta Accumulation and Improves Brain Function in a Mouse Model of A-Beta Amyloidosis." J. Neurosci. 34(21):7281-7292.
Liu, Yuhua and Tang, Chongren. (2012). "Regulation of ABCA1 Functions by Signaling Pathways." Biochim Biophys Acta. 1821(3): 522-529.
Mahley, R.W., et al. (2006). "Putting cholesterol in its place: apoE and reverse cholesterol transport." J. Clin. Invest.116:1226-1229.
Mawuenyega, K.G., et al. (2010). "Decreased Clearance of CNS beta-Amyloid in Alzheimer's Disease." Science 330:1774.
Raber, J., et al. (2004). "ApoE genotype accounts for the vast majority of AD risk and AD pathology." Neurobiology of Aging 25:641-650.
Thorngate, F.E., et al. (2000). "Low Levels of Extrahepatic Nonmacrophage ApoE Inhibit Atherosclerosis Without Correcting Hypercholesterolemia in ApoE-Deficient Mice." Arterioscler Thromb Vasc Biol. 20:1939-1945.
Tokuda, T., et al. (2000). "Lipidation of apolipoprotein E influences its isoform-specific interaction with Alzheimer's amyloid beta peptides." Biochem. J. 348:359-365.
Buttini, M., et al. (2000). "Dominant Negative Effects of Apolipoprotein E4 Revealed in Transgenic models of Neurodegenerative Disease." Neuroscience 97(2):207-210.
Michaelson, D.M. (2014). "APOE E4: The most prevalent yet understudied risk factor for Alzheimer's disease." Alzheimer's & Dementia 10: 861-868.
Brawley, J., "Design, synthesis and screening of apolipoprotein E (APOE) inhibitors based on aryl-amide and -sulfonamide scaffolds," *Thesis, California State University, Fresno, CA.*, Dated Aug. 2015, Publicly available Jan. 20, 2016, 76 pages.
Brown and Goldstein., "A receptor-mediated pathway for cholesterol homeostasis," *Science.*, 232(4746):34-47, Apr. 4, 1986.
Holtzman et al., "Expression of human apolipoprotein E reduces amyloid-β deposition in a mouse model of Alzheimer's disease," *J Clin Invest.*, 103(6):R15-R21, Mar. 15, 1999.
Kim et al., "Anti-apoE immunotherapy inhibits amyloid accumulation in a transgenic mouse model of Aβ amyloidosis," *J Exp Med.*, 209(12):2149-2156, 2012.
Kumar et al., "Effect of novel N-aryl sulfonamide substituted 3-morpholino arecoline derivatives as muscarinic receptor 1 agonists in Alzheimer's dementia models," *Bioorg Med Chem.*, 16:5157-5163, 2008.
Wahrle et al., "Overexpression of ABCA1 reduces amyloid deposition in the PDAPP mouse model of Alzheimer disease," *J Clin Invest.*, 118(2):671-682, Feb. 1, 2008.

* cited by examiner

METHOD OF INHIBITING APOLIPOPROTEIN-E EXPRESSION WHILE INCREASING EXPRESSION OF AT LEAST ONE OF LDL-RECEPTOR PROTEIN OR ABCA1 PROTEIN COMPRISING ADMINISTERING A SMALL COMPOUND

BACKGROUND OF THE INVENTION

Alzheimer's Disease is a common form of dementia associated with memory loss, intellectual function decline, depression, and disorientation. Alzheimer's Disease affects more than 5 million people in the United States and costs over $200 billion every year. (Alzheimer's Association, *The Journal of the Alzheimer's Association* (2012) 8: 131-168.) It is found in 13% of the population over the age of 65 and 45% of the population over the age of 85. (Alzheimer's Association, *The Journal of the Alzheimer's Association* (2012) 8: 131-168.) With a rapidly aging American population, prevalence of Alzheimer's Disease is expected to increase 2.5-fold to 13 million people in the United States in the next few decades. (Hebert et al., *Arch Neurol* (2003) 60: 1119-1122.) Alzheimer's Disease will continue to be a major and expensive health crisis.

Alzheimer's Disease is typified by increased deposition of amyloid beta plaques and neurofibrillary tangles in the brain. More than 95% of the cases are considered "sporadic" and affect individual older than 65 years of age (late-onset). These cases are distinguished from the rare, early-onset, genetically-linked cases where production and deposition of amyloid beta plaques is higher. (Bateman et al., *Alzheimer's Res Ther.* (2011) 3: 1-13). Individuals with late-onset Alzheimer's Disease produce amyloid beta plaques at a normal rate and level, but have a reduced ability to clear the amyloid beta plaques from the brain. (Mawuenyega, et al., *Science* (2010) 330: 1774.)

Apolipoprotein-E (apoE) is a cholesterol- and lipid-carrier that has been implicated in aging, atherosclerosis and several neurological diseases including Alzheimer Disease. (Mahley, et al., *J Clin Invest* (2006) 116: 1226-9, Thorngate, et al., *Vasc Biol* (2000) 20: 1939-45, Fullerton, et al., *Exp Neurol* (2001) 169: 13-22, Ji, et al., *Neuroscience* (2003) 122: 305-15, and Dergunov, et al., *Biochemistry* (Mosc) (2006) 71: 707-12.) ApoE genotype is the biggest risk factor for Alzheimer's Disease and may account for 60%-90% of the genetic variance associated with Alzheimer's Disease. (Raber, et al., *Neurobiol Aging* (2004) 25: 641-50.)

There are three common isoforms (alleles) of apoE in humans: apoE2, apoE3, and apoE4—which contribute to the pleiotropic effects observed in human cognition and neurodegenerative diseases. (Bales, et al., *Proc Natl Acad Sci USA* (1999) 96: 15233-3, Holtzman, et al., *J Clin Invest* (1999) 103: 15-21.) The risk for Alzheimer's Disease is two- and seven-fold higher in subjects that are heterozygous and homozygous, respectively, for apoE4. (Corder, et al., *Science* (1993) 261:921-3.) The age of disease onset is also accelerated by 6 years-8 years for each inherited copy of apoE4. (Corder, et al.) Several groups consider the apoE4 allele to be detrimental because the apoE4 protein aggregate with amyloid beta plaques more readily than other alleles and apoE4 protein is less effective at clearing the amyloid beta plaques from the brain (Tokuda, et al., *Biochem J* (2000) 348: 359-65, Castellano, et al., *Sci Transl Med* (2011) 3:895-7, and Buttini, et al., *Neuroscience* (2000) 97:207-10.).

These and other neurodegenerative effects have led some to conclude that apoE4 protein behaves like a "dominant-negative mutant," is a "neglected opportunity" for treatment of Alzheimer's Disease. (Michaelson, D. M. (2014) *Alzheimers Dement* 10:861-868.) Thus, there is a strong interest in the biomedical community to find therapies that can reduce apoE levels. Several animal studies clearly demonstrated that reduction of apoE4 and apoE3 reduce toxic amyloid accumulation. (Kim, J., et al. *J Neurosci.* (2011) 31:18007-18012; Bien-Ly, N., et al. *J Neurosci.* (2012) 32:4803-4811.)

High levels of low-density lipoprotein (LDL) and low levels of high-density lipoprotein (HDL) cholesterols are considered to be strong risk factors for cardiovascular diseases. The low density lipoprotein (LDL) receptor-related protein (LDLR) is a ubiquitously expressed endocytic receptor that binds a diverse group of ligands, including lipoproteins, lipoprotein lipase, proteases, protease inhibitors and protease:inhibitor complexes, bacterial toxins, viruses, and lactoferrin. Some of these macromolecules compete with each other for a common site on LDLR, while others bind to independent sites.

The gene encoding LDLR is an essential gene, because it participates in a wide range of biological processes. LDLR is a cell surface protein that plays an important role in mediating the removal of LDL cholesterol particles from the blood circulation (Brown M S and Goldstein J L. *Science.* (1986) 232(4746):34-47). Because LDL is causally associated with cardiovascular diseases, various strategies to decrease LDL cholesterols have been pursued for drug development.

Interestingly, apoE is implicated in atherosclerosis and Alzheimer's Disease (Mahley, et al., *J Clin Invest* (2006) 116: 1226-9.). In the brain, LDL receptor is the major apoE receptor. It has been demonstrated that reduction of apoE protein levels by overexpressing LDLR can dramatically inhibits toxic amyloid accumulation in the brains of a mouse model of Alzheimer's disease (Kim J, et al. *Neuron* (2009) 64:632-644). The finding that reduction of apoE levels can dramatically inhibit toxic amyloid accumulation is also supported in subsequent studies that genetically or pharmacologically inhibited apoE in the brain (Kim J, et al. *J Neurosci* (2011) 31:18007-18012; Kim J, et al. *J Exp Med* (2012) 209:2149-2156; Liao F, et al. *J Neurosci* (2014) 34:7281-7292.)

Like LDLR, the AbcA1 protein also plays a key role in regulating cholesterol in biological systems. HDL functions to transport cholesterol from peripheral cells to the liver by reverse cholesterol transport, a pathway that may protect against atherosclerosis by clearing excess cholesterol from arterial cells. A cellular ATP-binding cassette transporter (Abc) called AbcA1 mediates the first step of reverse cholesterol transport, the transfer of cellular cholesterol and phospholipids to lipid-poor apolipoproteins. Mutations in AbcA1 cause Tangier Disease (TD), a severe HDL deficiency syndrome characterized by accumulation of cholesterol in tissue macrophages and prevalent atherosclerosis.

Studies of TD heterozygotes revealed that AbcA1 activity is a major determinant of plasma HDL levels. Drugs that induce AbcA1 in mice increase clearance of cholesterol from tissues and inhibit intestinal absorption of dietary cholesterol. Multiple factors related to lipid metabolism and other processes modulate the tissue-specific expression of AbcA1. Therefore, as the primary gatekeeper for eliminating tissue cholesterol, AbcA1 has a major impact on cellular and whole body cholesterol metabolism and plays an important role in protecting against cardiovascular disease and Alzheimer's disease. (Koldamova R, et al. *Neurobiol Dis* (2014) 72:13-21; Liu Y and Tang C. *Biochem Biophys Acta* (2012) 1821:522-529.)

Since the American population is aging, and the percentage of American people with Alzheimer's Disease is expected to increase, there is the urgent need to further develop small organic molecules that can be easily administered to prevent, slow or stop the progression of the disease. Organic molecules that control the biological amounts of apoE, LDLR, and/or AbcA1 produced in mammalian systems would be of interest in light of the prior art.

The "Background of the Invention" section is provided for background information only, and is not an admission that any subject matter or references described in this section constitutes prior art to the present disclosure.

SUMMARY OF THE INVENTION

The present invention includes a method for decreasing expression of apolipoprotein E and increasing expression of at least one of either LDL-receptor protein or AbcA1 protein. The method involves the following steps: (1) selecting mammalian cells expressing apolipoprotein E and at least one of either LDL-receptor protein or AbcA1 protein, and (2) contacting the mammalian cells with an effective amount of a compound having general formula (I) in an amount sufficient to decrease expression of the apolipoprotein E and increase expression of at least one of the LDL-receptor protein or the AbcA1 protein in the mammalian cells. General formula (I) is shown here:

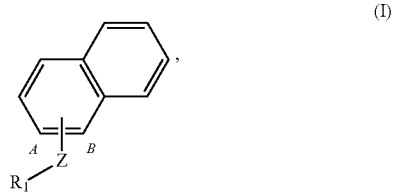

(I)

wherein Z may be at either position A or position B and may be selected from the group consisting of: $CH_2$, CO, or $SO_2$, and $R_1$ may be selected from the group consisting of:

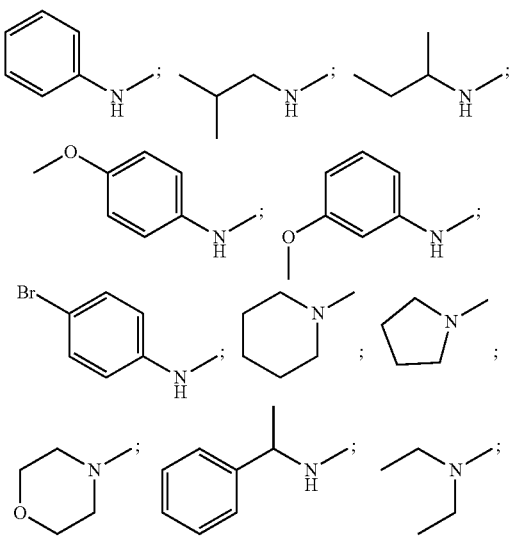

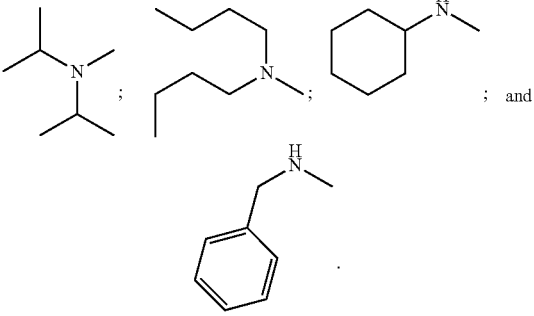

In another aspect of the invention, in the method described above utilizing the compound having a structure expressed as general formula (I), the selecting step selects for mammalian cells expressing apolipoprotein E, LDL-receptor protein, and AbcA1 protein, and the method decreases apolipoprotein E and increases expression of both the LDL-receptor protein and the AbcA1 protein. In still another aspect of the invention, in the method described above utilizing the compound having a structure expressed as general formula (I), the effective amount is 10 μM.

In yet another aspect of the invention, in the method described above utilizing the compound having a structure expressed as general formula (I), the method decreases expression of apolipoprotein E and increases expression of AbcA1, and the Z is located at position A and is $SO_2$, and the $R_1$ is

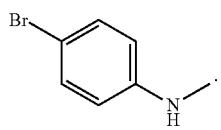

In one other aspect of the invention, in the method described above utilizing the compound having a structure expressed as general formula (I), the method decreases expression of apolipoprotein E and increases expression of LDL-receptor protein, and the Z is located at position A and is $CH_2$, and the $R_1$ is

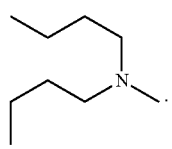

The invention also includes a method for decreasing expression of apolipoprotein E and increasing expression of at least one of LDL-receptor protein or AbcA1 protein by mammalian cells including the following steps: (1) selecting mammalian cells expressing apolipoprotein E and at least one of LDL-receptor protein or AbcA1 protein; and (2) contacting the mammalian cells with an effective amount of a compound having general formula (II) in an amount sufficient to decrease expression of the apolipoprotein E and increase expression of at least one of the LDL-receptor protein or AbcA1 protein in the mammalian cells. General formula (II) is shown here:

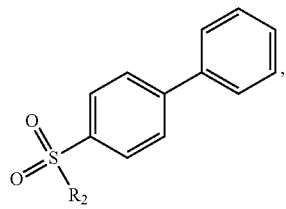

wherein $R_2$ may be a member selected from the group consisting of:

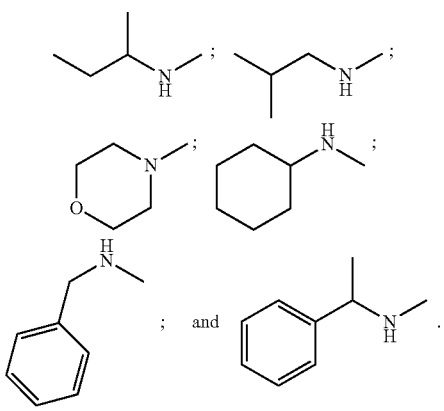

In another aspect of the invention, in the method described above utilizing the compound having a structure expressed as general formula (II), the selecting step selects for mammalian cells expressing apolipoprotein E, LDL-receptor protein, and AbcA1 protein, and the method decreases apolipoprotein E and increases expression of both the LDL-receptor protein and the AbcA1 protein. In still another aspect of the invention, in the method described above utilizing the compound having a structure expressed as general formula (II), the effective amount is 10 μM.

In another aspect of the invention, in the method described above utilizing the compound having a structure expressed as general formula (II), the method decreases expression of apolipoprotein E and increases expression of AbcA1, and the $R_2$ is

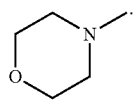

In still another aspect of the invention, in the method described above utilizing the compound having a structure expressed as general formula (II), the method decreases expression of apolipoprotein E and increases expression of LDL-receptor protein, and the $R_2$ is

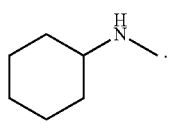

DETAILED DESCRIPTION OF THE INVENTION AND PREFERRED EMBODIMENTS

Figure 1A:
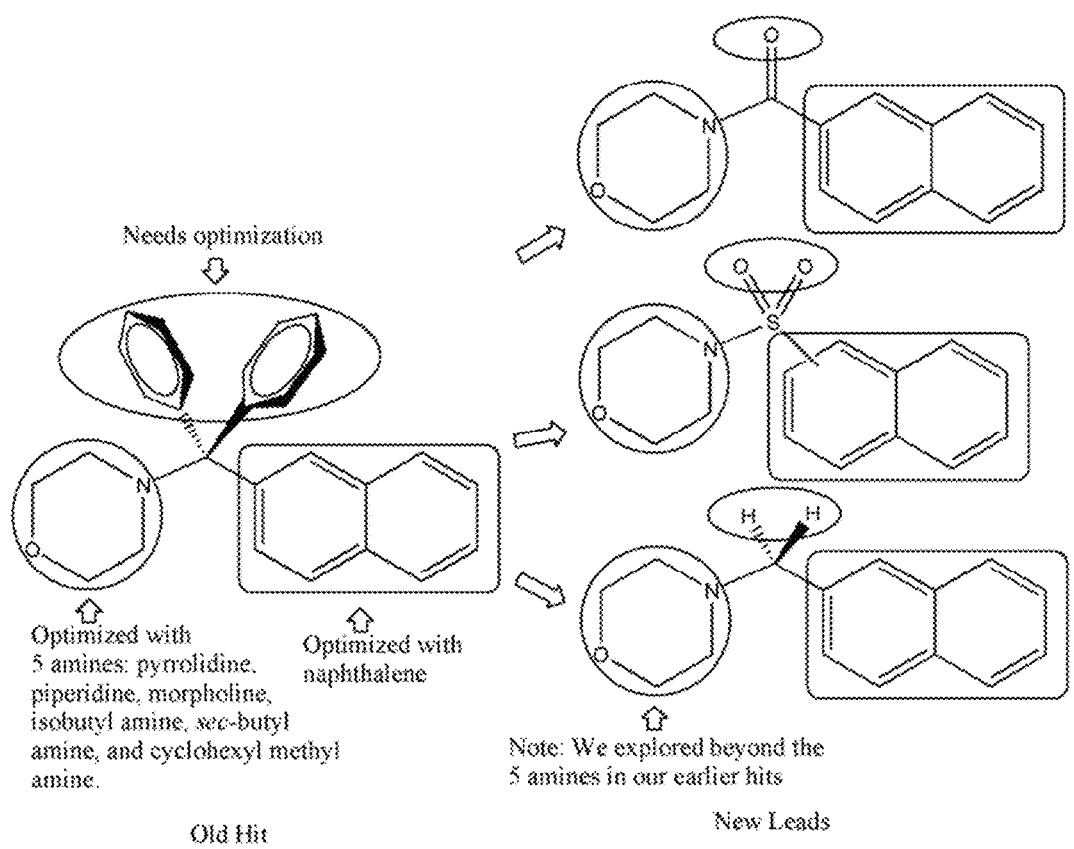
FIGS. 1A and 1B each show a scheme explaining how triarylmethyl amine compounds are changed to carboxamide, sulfonamide, and methyl amine compounds.

The present invention relates to small organic compounds and methods for decreasing the expression of apolipoprotein E (apoE) and for increasing the expression of at least one of LDLR and/or AbcA1 by mammalian cells.

The present invention relates to a number of small-molecule compounds which are capable of decreasing the expression levels of apoE by mammalian cells and for increasing the expression of at least one of LDLR and/or AbcA1 by mammalian cells when the compounds are administered in effective amounts. These small-molecule compounds are structurally described as carboxamides, sulfonamides, or arylmethyl amines and may have a scaffold structure represented by the general structure (I) or (II):

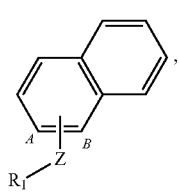

wherein Z may be at either position A or position B and may be selected from the group consisting of: $CH_2$ (arylmethyl amines), CO (carboxamides), and $SO_2$ (sulfonamides).

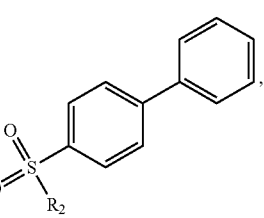

wherein compounds contain a biphenyl aryl unit containing a secondary or tertiary sulfonamide functionality. The amines contributing from the other end contain aliphatic, aryl, cyclic, and chiral groups.

A. Definitions

The term "selecting" as used herein includes both identifying an item and also accessing item. The step of selecting mammalian cells includes identifying specific mammalian cells having the described characteristics and then obtaining access to those mammalian cells.

The term "decreasing" as used herein is used interchangeably with the following: reducing, lowering, inhibiting, slowing, stopping, obstructing, impeding, and preventing.

The term "increasing" as used herein is used interchangeably with the following: amplifying, escalating, enhancing, multiplying, and adding to.

The term "expression" as used herein defines the process of gene expression including one, some or all of the following steps: transcription, RNA splicing, RNA stabilization, translation, and post-translational modification.

The term "contacting" as used herein may be used interchangeably with the following: passing over, incubating with, combining with, flowing over, mixing with, and adding to.

The phrase "effective amount" as used herein defines an amount of a given carboxamide compound administered to mammalian cells which results in an objectively quantifiable decrease in apoE protein production and an objectively quantifiable increase in at least one of LDLR and/or AbcA1 in at least some of those cells as observed or noted by a scientist, clinician, or other qualified observer of ordinary skill in the art.

The phrase "at least one of either" as used herein means either one of—or both of—two items described after the phrase at least one of either", the two items being separated by the term "or."

B. Naphthalene-Based Carboxamide Compounds

Carboxamide compounds have a naphthalene unit with the carboxamide located at the 2-position. The amines on the other end of the secondary and tertiary amides consist of acyclic and cyclic chains. In Table 1, the carboxamide compounds are compound nos. 88-92 and 98-101. The carboxamide compounds as disclosed in Table 1 have molecular weights ranging from about 213 kDa to about 361 kDa.

C. Naphthalene-Based Sulfonamide Compounds

Naphthalene-based sulfonamide compounds contain a naphthalene ring substituted at 1 or 2 position with secondary or tertiary sulfonamide functionality utilizing primary and secondary amines. Aliphatic, aromatic, acyclic, and cyclic amines have been used for the construction of these molecules having a scaffold structure represented by general formula (I). In Table 1, the naphthalene sulfonamide compounds are compound nos. 93-97 and 102-131. The naphthalene sulfonamide compounds as disclosed in Table 1 have molecular weights ranging from about 261 kDa to about 326 kDa.

D. Biphenyl-Based Sulfonamide Compounds

For the sulfonamide compounds described as having a scaffold structure represented by general formula (II), this series contains a biphenyl aryl unit with a sulfonamide functionality. The amines contributing to the molecules are diverse containing aliphatic, aromatic, acyclic, and cyclic units. In Table 1, the biphenyl-based sulfonamide compounds are compound nos. 132-137. The biphenyl-based sulfonamide compounds as disclosed in Table 1 have molecular weights ranging from about 289 kDa to about 337 kDa.

E. Naphthalene-Based Arylmethyl Amine Compounds

For the arylmethyl amine compounds described as having a scaffold structure represented by general formula (I), the 2-naphthyl unit is spaced with a methylene unit from a tertiary amine containing cyclic and symmetrical acyclic hydrocarbon moieties. In Table 1, the aryl methyl amine compounds are nos. 138-141. The arylmethyl amine compounds as disclosed in Table 1 have molecular weights ranging from about 213 kDa to about 279 kDa.

F. Designing the Claimed Compounds

The small organic compounds consisting of carboxamide, sulfonamide, and arylmethyl units were identified as candidates for inhibiting apoE expression in an initial pilot screening. The initial apoE screening was performed on a small library of compounds. The goal was to screen a collection of hydrocarbon-rich small organic molecules based upon simple scaffolds that could be easily synthesized. The basic structures of these small organic molecules were derived through Structure-Activity Relationship (SAR) studies from triarylmethyl amine scaffolds (U.S. Pat. Nos. 8,633,195 and 8,897,507).

The primary objective of the small organic molecule design was to retain those segments of the triarylmethyl amine scaffold that were verified to contribute to the desired biological activity (as shown in U.S. Pat. Nos. 8,633,195 and 8,897,507), but also to increase the overall chemical stability of these compounds. The triarylmethyl amines are acid-sensitive and therefore suffer from both laboratory chemical instability and are anticipated to have pharmacokinetic instability as well. These molecules are also very lipophilic with high clogP values way above 5. Thus, efforts were made to incorporate chemical and subsequently pharmacokinetic stability while increasing drug-likeness by reducing lipophilicity.

Figure 1B:
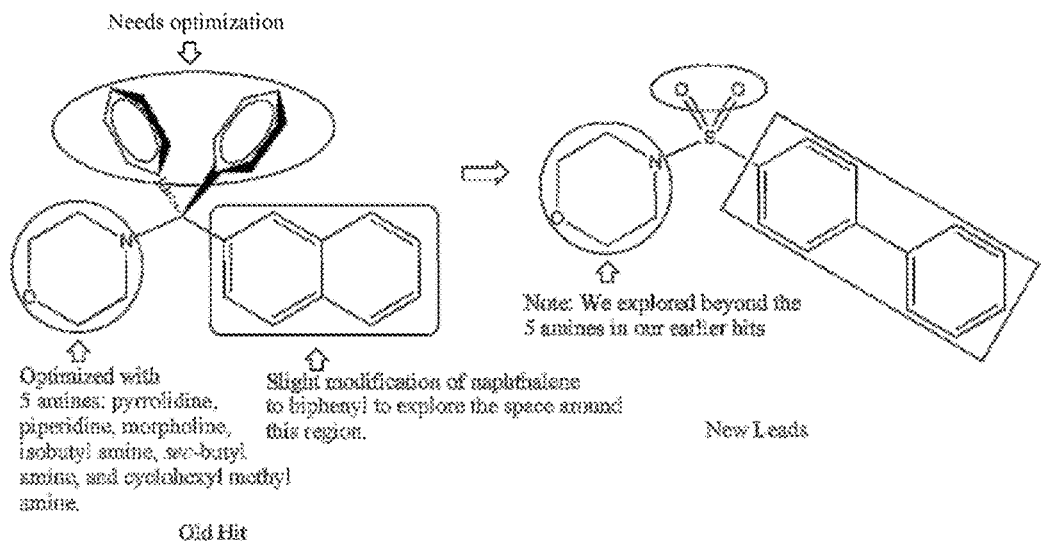

As shown in FIGS. 1A and 1B, the aryl rings in the triarylmethyl amine scaffold demanded further scrutiny because out of the four chemical zones or regions, the amines and the larger aromatic rings were explored more elaborately than the two phenyl rings. The research team was curious to learn more about the space occupied by the phenyl rings and to what extent the desired biological effects would alter by structural changes made there. This further scrutiny eventually led to the optimization of the aryl rings, coupled with an amine side group, and either the naphthalene or the biphenyl side group. The optimization of the aryl rings and the coupling of the new side groups led to the new four new scaffold structures (new leads): naphthalene-based carboxamide compounds, naphthalene-based sulfonamide compounds, biphenyl-based sulfonamide compounds, and naphthalene-based arylmethyl amine compounds.

As shown in FIG. 1A, the naphthalene-based carboxamide compound was created by transforming the triarylmethyl amine by changing the two aryl rings into a carboxyl structure coupled with an amine structure and a naphthalene side group. In one embodiment, as shown in FIG. 1A, the amine group can be a morpholine.

As shown in FIG. 1A, the naphthalene-based sulfonamide compound was created by transforming the triarylmethyl amine by changing the two aryl rings and the connecting carbon into a sulfonamide structure coupled with an amine group and a naphthalene side group. In one embodiment, as shown in FIG. 1A, the amine group can be a morpholine.

As shown in FIG. 1A, the naphthalene-based arylmethyl amine compounds was created by transforming the triarylmethyl amine by changing the two aryl rings into two hydrogens coupled with an amine group and a naphthalene side group. In one embodiment, as shown in FIG. 1A, the amine group can be a morpholine.

As shown in FIG. 1B, the biphenyl-based sulfonamide compound was created by transforming the triarylmethyl amine by changing the two aryl rings and the connecting carbon into a sulfonamide structure coupled with an amine group and a biphenyl side group. In one embodiment, as shown in FIG. 1B, the amine group can be a morpholine.

Additional guidelines for our design philosophy encompassed the need for enhanced chemical and pharmacological stability, lower cLogP (reduced lipophilicity), and overall drug-likeness in the chemical structure. After the initial screening, the compounds listed in Table 1 were chosen to undergo further biological testing. The compound numbers associated with each compound structure is the identifying number for the compound during biological tests.

TABLE 1

Compound Structures with Compound Numbers

Compound No.

88

89

90

91

92

TABLE 1-continued

Compound Structures with Compound Numbers

Compound No.

93

94

95

96

97

98

99

100

101

TABLE 1-continued

Compound Structures with Compound Numbers

| Compound No. | Structure |
|---|---|
| 102 | N-phenyl naphthalene-2-sulfonamide |
| 103 | N-(4-bromophenyl) naphthalene-2-sulfonamide |
| 119 | 4-(naphthalen-1-ylsulfonyl)morpholine |
| 120 | N-(sec-butyl)naphthalene-1-sulfonamide |
| 121 | N-isobutylnaphthalene-1-sulfonamide |
| 122 | 1-(naphthalen-1-ylsulfonyl)piperidine |
| 123 | 1-(naphthalen-1-ylsulfonyl)pyrrolidine |
| 124 | N-cyclohexylnaphthalene-1-sulfonamide |
| 125 | N-benzylnaphthalene-1-sulfonamide |
| 126 | N,N-diethylnaphthalene-1-sulfonamide |
| 127 | N,N-dibutylnaphthalene-1-sulfonamide |
| 128 | N,N-dibutylnaphthalene-2-sulfonamide |
| 129 | N,N-diethylnaphthalene-2-sulfonamide |
| 130 | N,N-diisopropylnaphthalene-2-sulfonamide |
| 131 | N-(1-phenylethyl)naphthalene-2-sulfonamide |

TABLE 1-continued

Compound Structures with Compound Numbers

| Compound No. | Structure |
|---|---|
| 132 | (sec-butyl sulfonamide of biphenyl) |
| 133 | (isobutyl sulfonamide of biphenyl) |
| 134 | (morpholinyl sulfonamide of biphenyl) |
| 135 | (benzyl sulfonamide of biphenyl) |
| 136 | (cyclohexyl sulfonamide of biphenyl) |
| 137 | (1-phenylethyl sulfonamide of biphenyl) |
| 138 | (morpholinylmethyl naphthalene) |
| 139 | (dibutylaminomethyl naphthalene) |
| 140 | (diethylaminomethyl naphthalene) |
| 141 | (piperidinylmethyl naphthalene) |

Altogether, 41 different carboxamide, sulfonamide, and arylmethyl amine compounds are included in Table 1. As shown in Table 1, the 6 secondary carboxamide compounds include 88, 89, 98, 99, 100, and 101 consisting aliphatic and aromatic groups, viz., isobutyl, sec-butyl, phenyl, and substituted phenyl groups with both electron-withdrawing and donating effects. The tertiary carboxamide compounds 90, 91, and 92 contain aliphatic 5- and 6-membered rings. The sulfonamide molecules consist 1- and 2-substituted naphthyl sulfonyl and 4-substituted biphenyl groups. Secondary and tertiary sulfonamides with acyclic, cyclic, aliphatic, a few aromatic amines primarily populate the group. Compounds 93-97 and 128-131 are all derived from 2-naphthyl sulfonyl chlorides with primary and cyclic secondary amines. Compounds 102 and 103 utilize the same sulfonyl segment with aryl amines. Compounds 119-127 are 1-naphthyl sulfonyl chloride derivatives containing overlapping primary and secondary amines from both aliphatic and aromatic families. A few biphenyl target sulfonamides, compounds 132-137 were synthesized with similar amine counterparts as the other sulfonamides described.

G. Synthesis of the Carboxamide Compounds

Figure 2:
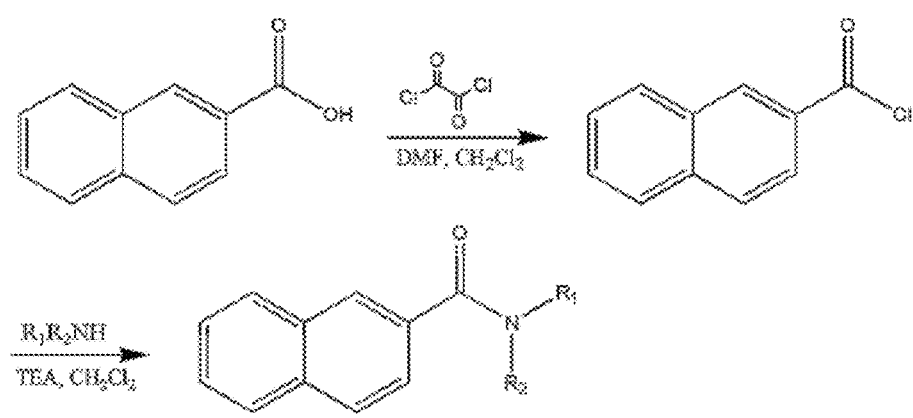
FIG. 2 shows a scheme for synthesizing carboxamide compounds.

As shown in FIG. 2, the synthesis of carboxamide compounds starts with the aryl carboxylic acid and oxalyl chloride in the presence of catalytic amount of dimethyl formamide (DMF) to generate the acid chloride. The reaction mixture is stirred under inert atmosphere for 2 hours with 2 equivalents of oxalyl chloride and catalytic amount of DMF at room temperature. The resulting solution was briefly washed with ice-cold water, brine, and dried prior to removing the solvent under reduced pressure. The crude acid chloride is directly used for the next reaction with an appropriate amine without further purification and/or characterization. The acid chloride was reacted with slight excess (approximately 5%) of the primary or secondary amine in the presence of 2 equivalents of triethyl amine in methylene chloride as a solvent for 15 hours.

The resulting mixture is subsequently washed with water, mild acid, base, and brine. Upon drying with an anhydrous drying agent ($Na_2SO_4$) and filtration the resulting solution was stripped off the solvent to yield the crude amide. The crude was further purified by crystallization or medium-pressure column chromatography or preparatory thin layer chromatography (PTLC).

H. Synthesis of the Sulfonamides

Figure 3:
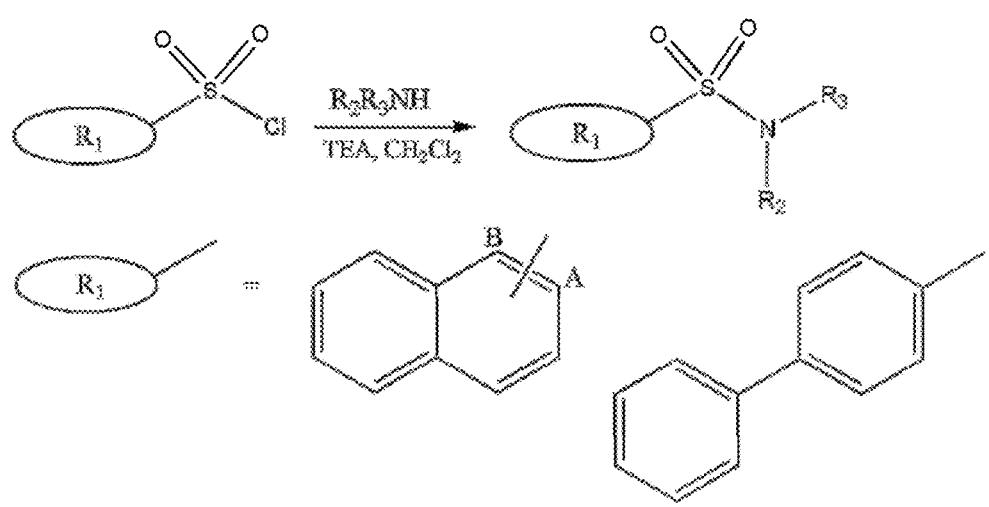
FIG. 3 shows a scheme for synthesizing the sulfonamide compounds.

FIG. 3 describes the general synthesis of sulfonamides. The commercial aryl sulfonyl chlorides were directly reacted with the primary or secondary amines in methylene chloride in the presence of 2 equivalents of triethyl amine at room temperature. The crude products were further purified by crystallization or medium-pressure column chromatography or preparatory thin layer chromatography (PTLC).

I. Synthesis of the Arylmethyl Amines

Figure 4:
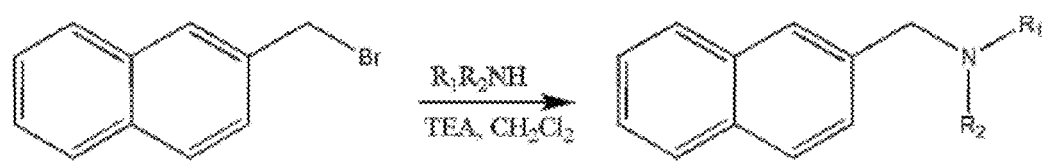
FIG. 4 shows a scheme for synthesizing the aryl methyl amine compounds.

FIG. 4 described the synthesis of the arylmethyl amines by alkylating primary arylmethyl bromides with symmetrical secondary amines. The reactions were carried out in methylene chloride in the presence of 2 equivalents of triethyl amine at room temperature for 15 hours. The crude tertiary amine products were purified by chromatography.

One of ordinary skill in the art, based on the synthesis description herein, can formulate the described carboxamide, sulfonamide, and methylaryl amine compounds using conventional synthetic chemistry techniques. The following specific examples, which describe the synthesis of several compounds of this invention, are to be construed as merely illustrative and not limiting of the disclosure in any way.

EXAMPLE 1

Synthesis of Naphthalene-2-Carboxylic Acid Sec-Butylamine (Shown as Compound 88 in Table 1)

The synthesis of an amide is a well-established procedure that is illustrated in FIG. 2. The procedure used to synthesize these preliminary molecules is based on a procedure described by Koch, Lloyd-Jones, et. al due to its simplicity and the chemicals available. The first step is to add the 2-naphthoic acid (0.50 g, 2.9 mmol) into a dry round bottom flask. The 2-naphthoic acid was then dissolved in dichloromethane (15 mL) using a magnetic stir bar and stirring plate. One drop of dimethylformamide (DMF) and oxalyl chloride (0.48 mL, 3.48 mmol) was then added slowly and the round bottom flask sealed with a water condenser and drying tube packed with anhydrous $CaCl_2$. The solution was allowed to react for 24 hours at room temperature.

When the reaction period was reached, the solvent of the solution was evaporated under vacuum to remove the excess oxalyl chloride and DMF. The resulting solid was dissolved in dichloromethane and cooled to zero degrees Celsius. Triethylamine (1.2 eq.) and the desired amine (0.44 mL, 4.35 mmol) were added dropwise into the cooled solution. The solution was allowed to react for 4 hours. The solution was then washed with 10% NaOH, 10% HCl, $H_2O$, and the collected organic layer was dried with anhydrous $MgSO_4$ to yield crude product. Column chromatography using 200-400 mesh silica gel with ethyl acetate/hexane mixture as an eluent (gradient, 10% to 40%) yielded 0.45 g of pure product (59%).

The following are the $^1$H-NMR, $^{13}$C-NMR and IR Spectra Results for carboxylamide naphthalene-2-carboxylic acid sec-butylamide (88): $^1$H NMR (300 MHz, $CDCl_3$) δ 8.28 (s, 1H), 7.97-7.80 (m, 4H), 7.65-7.49 (m, 2H), 6.03 (d, J=6.75 Hz, 1H), 4.21 (sep, J=4.83 Hz, 1H), 1.65 (quin, J=7.08 Hz, 3H), 1.30 (d, J=6.6 Hz, 2H), 1.03 (t, J=7.5 Hz, 3H); $^{13}$C NMR (300 MHz/$CDCl_3$) δ 167.09 (C), 134.75, 132.76, 132.41, 128.97, 128.51, 127.85, 127.62, 127.23, 126.82, 123.72, 47.35, 29.97, 20.68, 10.60; IR v-($cm^{-1}$): 3264, 2960, 2926, 2872, 1624, 1541, 1308, 1156, 866, 827, 775, 741, 706, 588.

EXAMPLE 2

General Synthesis of all Secondary and Symmetrical Tertiary Sulfonamides

The synthesis of secondary or symmetrical tertiary sulfonamides is follows a similar procedure to the synthesis of carboxylamide and is illustrated in FIG. 3. The corresponding sulfonyl chloride (3.0 mmol) was added to a 25 mL round bottom flask. Dichloromethane (5 mL) was then added to the round bottom flask. The contents were stirred in order to dissolve sulfonyl chloride into the solution using a magnetic stir bar. The solution was subsequently cooled to zero degrees Celsius and triethylamine (1.2 eq.) and the desired amine (1.5 eq.) were added dropwise into the mixture. The solution was allowed to stir for 4 hours and then washed with 10% NaOH, 10% HCl, $H_2O$, and the collected organic layer was dried with anhydrous $MgSO_4$ to yield the crude product. The crude sulfonamide was further purified by recrystallization or medium-pressure column chromatography using 230-400 mesh silica gel and ethyl acetate:hexane eluent mixture (10%-40% gradient) to yield pure target molecules.

The following are the $^1$H-NMR, $^{13}$C-NMR and IR Spectra Results for naphthalene-1-sulfonic acid dibutylamide (Compound No. 127). $^1$H NMR (300 MHz, $CDCl_3$) δ 8.67 (d, J=7.8 Hz, 1H), 8.20 (d, J=6.1 Hz, 1H), 8.05 (d, J=8.3 Hz, 1H), 7.92 (d, J=7.2 Hz, 1H), 7.70-7.50 (m, 3H), 3.28 (t, J=7.68 Hz, 4H), 1.46 (quin, J=7.4 Hz, 4H), 1.20 (sex, J=7.5, 4H), 0.81 (t, J=7.4 Hz, 6H); $^{13}$C NMR (300 MHz/$CDCl_3$) δ 135.49 (C), 134.49, 134.02, 129.58, 128.87, 127.95, 126.84, 125.27, 124.14, 46.61, 30.25, 19.94, 13.70; IR v-($cm^{-1}$): 2957, 2931, 2871, 1507, 1459, 1319, 1155, 1127, 1024, 918, 770, 582.

EXAMPLE 3

General Synthesis of Arylmethyl Amines

The four tertiary arylmethyl amines were synthesized by nucleophilic substitution reaction of 2-naphthylmethyl bromides with secondary amines.

2-Naphthylmethyl bromide (3 mmol) was reacted with a secondary amine (1.2 eq.) in the presence of triethyl amine (1.5 eq.) in dichloromethane (10 mL) in a 25 mL round-bottomed flask. The reaction was carried out at room temperature under inert atmosphere for 15 h. The reaction mixture was washed with water (3×10 mL), dried with anhydrous sodium sulfate, filtered. The solvent was removed under reduced pressure to yield the crude tertiary amine product as an oil. The crude product was further purified by medium-pressure column chromatography using 23-400 mesh silica gel and ethyl acetate:hexanes solvent mixture (1%-25%) with 1% triethyl amine. The triethyl amine was used to prevent streaking of the product.

C. Biological Effects of the Claimed Compounds on Mammalian Cells

The compounds of this invention have been found to be potent inhibitors of apoE expression while increasing the expression of one of LDLR or AbcA1, or both LDLR and AbcA1. As such, this invention contemplates using the compounds of this invention (as listed in Table 1), to inhibit apoE expression in mammalian cells, either in vivo or in vitro, while increasing the expression of at least one of LDLR or AbcA1.

We suspect that LDLR and AbcA1 work together to regulate apoE levels and lipidation. If LDLR and AbcA1 work together to decrease or inhibit apoE levels and lipidation then this would be ideal for decreasing the risk of a patient developing Alzheimer's Disease. This synergy between LDLR and AbcA1 may decrease the likelihood of a patient developing Alzheimer's Disease by facilitating the removal of toxic amyloid β proteins. Because amyloid β protein is the initial trigger of Alzheimer's Disease, reducing amyloid β level will act at the initiation step of pathogenesis and prevent downstream pathological alterations in the brain.

i. Carboxamide, Sulfonamide, and Arylmethyl Compounds Decrease or Inhibit apoE3 Expression.

Treatment of mammalian cells with the claimed compounds can lead to a decreased amount of apoE protein in the treated cells. In some experiments described in this section, treatment of mammalian cells with the claimed compounds specifically can lead to a decreased amount of apoE3 protein in the treated cells.

Reducing the levels of human ApoE protein levels attenuates amyloid accumulation in mouse models of Alzheimer's Disease. (Kim, J., et al. (2011) *J Neurosci.* 31:18007-18012; Bien-Ly, N., et al. (2012) *J Neurosci.* 32:4803-4811.) Experiments were set up to test whether the claimed carboxamide compounds, sulfonamide compounds, and arylmethyl amine compounds listed in Table 1 inhibit or decrease apoE3 expression in mammalian cells.

ApoE inhibition can be readily determined by any one of several assays and techniques known to those of ordinary skill in the art, including the enzyme-linked immunosorbant assay (ELISA). In the experimental results shown in Table 2 and FIG. 5, the ELISA assay was carried out on cortical astrocyte cells from mice. Astrocyte cells produce apoE, LDLR and AbcA1 proteins. Astrocyte cells are the primary producers of apoE protein in the brain and expression of apoE in astrocytes increases with age, as well as progression of Alzheimer's Disease and/or brain injury (Bien-Ly, et al, *J Neurosci* (2012) 32:4803-11).

The experiments involved treating mouse cortical astrocyte cells with the claimed compounds at 10 μM concentration for an incubation time of 24 hrs. DMSO solvent was used as a negative control, because the compounds were dissolved in DMSO when applied to the cells.

Figure 5:
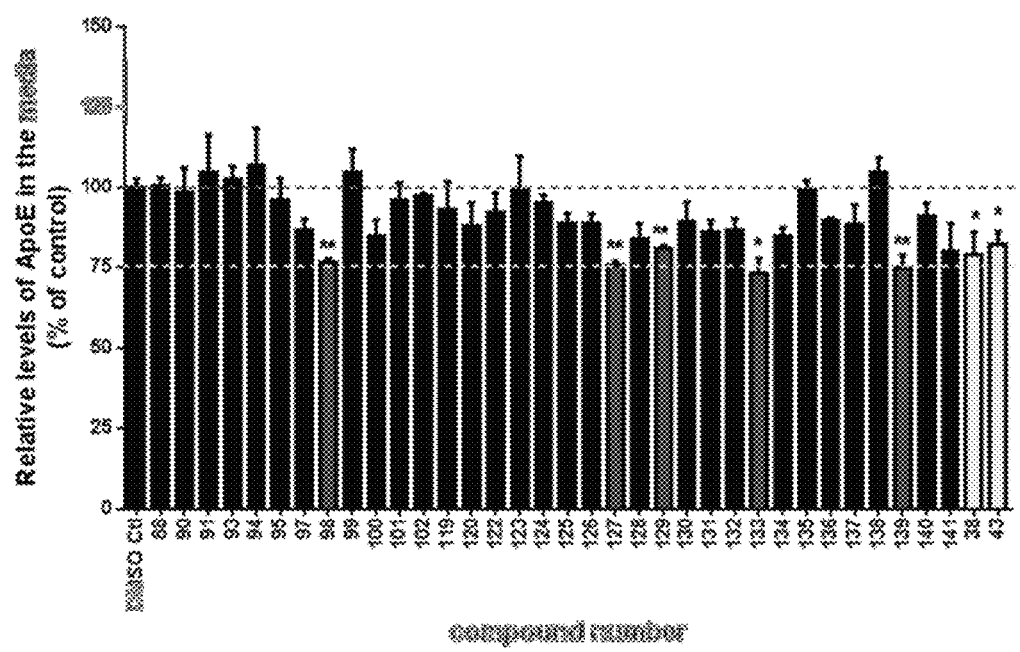
FIG. 5 shows a bar graph depicting the effect of the identified compounds at a concentration of 10 mM on apoE production in mouse brain cells (E3 astrocyte cells). Each of the identified compounds has a scaffold structure shown by either general formula I or general formula II. The compounds labeled 38 and 43 have a triarylmethyl amine scaffold structure.

Table 2 and FIG. 5 shows the biological results of the carboxamide compounds, sulfonamide compounds and arylmethyl amine compounds by compound number—affiliated with the respective compound structure in Table 1. For the experimental results shown in Table 2 and FIG. 5, the identified compounds were tested for biological effects in mouse cortical astrocyte cells in an ELISA assay. The ELISA technique involves immobilizing an apoE-specific capture antibody to a 96-well plate, addition of sample (conditioned medium from mouse cortical astrocyte cells treated with the compound for 24 hours), and detection of the bound apoE using a second apoE-specific biotinylated antibody and streptavidin-HRP.

The ELISA's used in the experiments described were based on two ApoE antibodies, from Novus NB110-60531 and Meridian Life Science (K74180B). The Mabtech ELISA kit detects the presence of the three apoE isoforms: apoE2, apoE3, and apoE4.

EXAMPLE NO. 4

Compounds Administered to Cortical Astrocyte Cells and Analyzed by ELISA to Determine the Effects on ApoE3 Levels To obtain the data shown in Table 2 and FIG. 5, the mouse cortical astrocyte cells were maintained in DMEM medium (Invitrogen) supplemented with 10 mM HEPES, 1 mM sodium pyruvate, 4.5 g/L glucose, 1% penicillin/streptomycin, and 10% fetal bovine growth serum (Invitrogen) at 37° C., with 5% $CO_2$.

All compounds identified by number in Table 2 and FIG. 5 (compound number corresponding to the respective structure shown in Table 1) were individually dissolved in DMSO at a stock concentration of 1004 and individually tested. The cells ($6×10^4$ cells/24-well plate) were grown for 1 day in RPMI, followed by a 24 hour equilibration in serum-free Opti-MEM (Life Technologies). Treatments were carried out in triplicate with 100 μM of fresh Opti-MEM containing 10 μM of compound or vehicle (0.1% DMSO) for 24 hours. Conditioned medium from these samples were then diluted 2-fold with incubation buffer (PBS+0.05% Tween-20+0.1% BSA) and analyzed with a human apoE HRP ELISA based on Novus NB110-60531 and Meridian Life Science (K74180B) antibodies. ApoE concentration in the sample was calculated based on a standard curve derived using known amounts of purified apoE (from Biodesign).

The protein levels in the cells in the 24-well plates were measured using BCA Protein Assay Kit (from Pierce) and used to normalize the data. This normalization step provides an effective control for the cell culture conditions and experimental compounds. Sample apoE3 concentrations were represented relative to the DMSO treated cells.

Results for each set of compounds tested in parallel (n=3) were analyzed by a two-tailed t-test. The bars in FIG. 5 reflect the respective mean level apoE3 in the media for each compound with an indication of one standard of the mean.

TABLE 2

Effects of Claimed Compounds on ApoE3 Levels in Mammalian Cells

| | ApoE3 Levels in Cell Media | | | |
|---|---|---|---|---|
| Compound No. | Test 1 | Test 2 | Test 3 | Average of Three Tests |
| DMSO control | 104.2867 | 101.1855 | 94.5278 | 100 |
| 88 | 104.1856 | 95.94471 | 101.9038 | 100.678 |
| 89 | 110.4906 | 131.1414 | 147.9187 | 129.8502 |
| 90 | 90.22193 | 91.68984 | 113.8441 | 98.58529 |
| 91 | 126.8225 | 87.20131 | 99.94446 | 104.6561 |
| 92 | 128.0284 | 127.4327 | 89.93698 | 115.1327 |
| 93 | 103.3801 | 109.2249 | 95.25397 | 102.6197 |
| 94 | 99.11679 | 91.64069 | 129.7451 | 106.8342 |
| 95 | 86.86764 | 92.01868 | 109.5 | 96.12877 |
| 96 | 104.9618 | 132.594 | 118.4035 | 118.6531 |
| 97 | 90.21957 | 90.28416 | 80.08308 | 86.86227 |
| 98 | 74.21887 | 79.00266 | 75.5362 | 76.25258 |
| 99 | 106.2723 | 116.3467 | 91.14867 | 104.5892 |
| 100 | 91.06144 | 75.01479 | 88.87806 | 84.98476 |
| 101 | 93.29305 | 88.20501 | 106.6434 | 96.04715 |
| 102 | 95.99241 | 98.80215 | 96.62006 | 97.13821 |
| 103 | 84.77692 | 113.1319 | 129.4577 | 109.1222 |
| 119 | 110.6094 | 81.73117 | 87.289 | 93.20991 |
| 120 | 100.2942 | 88.30618 | 76.24577 | 88.28205 |
| 121 | 113.2938 | 128.755 | 98.9502 | 113.6663 |
| 122 | 100.1387 | 96.02251 | 80.1244 | 92.0952 |
| 123 | 85.68725 | 90.17963 | 120.6126 | 98.82649 |
| 124 | 96.7646 | 90.1191 | 98.41956 | 95.10109 |
| 125 | 82.43889 | 91.38652 | 92.50781 | 88.77774 |
| 126 | 93.70214 | 89.09737 | 84.65514 | 89.15155 |
| 127 | 75.35568 | 78.17972 | 73.66109 | 75.73216 |
| 128 | 85.62845 | 91.51279 | 74.78012 | 83.97379 |
| 129 | 80.4063 | 82.81916 | 80.19173 | 81.13906 |
| 130 | 89.05973 | 79.11883 | 100.0032 | 89.39392 |
| 131 | 78.37613 | 91.40717 | 87.92131 | 85.90154 |
| 132 | 81.50583 | 85.60579 | 93.42204 | 86.84455 |
| 133 | 81.61389 | 72.54003 | 65.40093 | 73.18495 |
| 134 | 81.06552 | 90.29737 | 82.88513 | 84.74934 |
| 135 | 93.55084 | 101.8388 | 102.6888 | 99.35948 |
| 136 | 89.57876 | 91.19713 | 88.40705 | 89.72765 |
| 137 | 79.41091 | 86.64903 | 99.82996 | 88.62997 |
| 138 | 103.8509 | 97.61428 | 113.0808 | 104.8487 |
| 139 | 67.21479 | 81.68683 | 75.43539 | 74.779 |

TABLE 2-continued

Effects of Claimed Compounds on
ApoE3 Levels in Mammalian Cells

| | ApoE3 Levels in Cell Media | | | |
|---|---|---|---|---|
| Compound No. | Test 1 | Test 2 | Test 3 | Average of Three Tests |
| 140 | 91.45573 | 97.9104 | 83.53577 | 90.9673 |
| 141 | 80.57078 | 95.08708 | 65.28588 | 80.31458 |
| Triarylmethyl Amine Compound No. 38 | 76.4862 | 92.34526 | 68.37921 | 79.07022 |
| Triarylmethyl Amine Compound No. 43 | 86.35254 | 74.71505 | 86.31501 | 82.46087 |

As shown in Table 2 and FIG. 5, some compounds effectively decrease apoE3 expression in mammalian cortical astrocyte cells. The DMSO sample serves as a control. On the graph shown in FIG. 5, the Y-axis shows the levels of apoE3 protein in the cell media as a percentage of the DMSO control. Continuing with FIG. 5, the black dotted line shows the reference line of 100% of the DMSO control. As shown in Table 2 and FIG. 5, there is less apoE3 in the media of mammalian cortical astrocyte cells treated with compound nos. 90, 95, 97, 98, 100-102, 119, 120, 122-134, 136, 137, 139-141 compared to mammalian cortical astrocyte cells treated with control DMSO. Therefore, compound nos. 90, 95, 97, 98, 100-102, 119, 120, 122-134, 136, 137, 139-141 all decrease apoE expression in mammalian cortical astrocyte cells compared to the control DMSO. Specifically, compound nos. 90, 95, 97, 98, 100-102, 119, 120, 122-134, 136, 137, 139-141 all decrease apoE3 expression in mammalian cortical astrocyte cells compared to the control DMSO.

The triarylmethyl amine compound nos. 38 and 43 have the structures listed in Table 3. Triarylmethyl amine compound nos. 38 and 43 also effectively decrease apoE expression—specifically, apoE3 expression—in mammalian cortical astrocyte cells. Triarylmethyl amine compound nos. 38 and 43 are disclosed and claimed in U.S. Pat. Nos. 8,633,195 and 8,897,507 and their effects are shown in Table 2 and FIG. 5 for comparison to the claimed compounds.

TABLE 3

Triarylmethyl Amine Compounds

| Compound No. | Triarylmethyl Amine Structure |
|---|---|
| 38 | 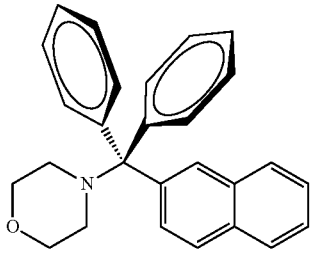 |
| 43 | 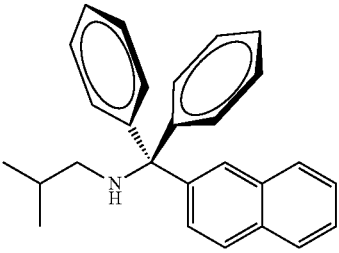 |

According to Table 2 and FIG. 5, apoE3 levels are about at least 10% less in the media of mammalian cortical astrocyte cells treated with compound nos. 97, 98, 100, 120, 125-134, 136, 137, 139, 141 compared to mammalian cortical astrocyte cells treated with control DMSO. Therefore, compound nos. 97, 98, 100, 120, 125-134, 136, 137, 139, 141 all decrease apoE expression in mammalian cortical astrocyte cells by at least about 10% compared to the control DMSO. Specifically, compound nos. 97, 98, 100, 120, 125-134, 136, 137, 139, 141 all decrease apoE3 expression in mammalian cortical astrocyte cells by at least about 10% compared to the control DMSO.

According to Table 2 and FIG. 5, apoE3 levels are about at least 18% less in the media of mammalian cortical astrocyte cells treated with compound nos. 98, 127, 129, 133, and 139 compared to mammalian cortical astrocyte cells treated with control DMSO. Therefore, compound nos. 98, 127, 129, 133, and 139 all decrease apoE expression in mammalian cortical astrocyte cells by at least about 18% compared to the control DMSO. Specifically, compound nos. 98, 127, 129, 133, and 139 all decrease apoE3 expression in mammalian cortical astrocyte cells by at least about 18% compared to the control DMSO.

According to Table 2 and FIG. 5, apoE3 levels are about at least 24% less in the media of mammalian cortical astrocyte cells treated with compound nos. 127, 133 and 139 compared to mammalian cortical astrocyte cells treated with control DMSO. Therefore, compound nos. 127, 133 and 139 decrease apoE expression in mammalian cortical astrocyte cells by at least about 24% compared to the control DMSO. Specifically, compound nos. 127, 133 and 139 decrease apoE3 expression in mammalian cortical astrocyte cells by at least about 24% compared to the control DMSO.

According to Table 2 and FIG. 5, apoE3 levels are about at least 25% less in the media of mammalian cortical astrocyte cells treated with compound nos. 133 and 139 compared to mammalian cortical astrocyte cells treated with control DMSO. Therefore, compound nos. 133 and 139 decrease apoE expression in mammalian cortical astrocyte cells by at least about 25% compared to the control DMSO. Specifically, compound nos. 133 and 139 decrease apoE3 expression in mammalian cortical astrocyte cells by at least about 25% compared to the control DMSO.

ii. Claimed Compounds Increase LDLR Expression

For a small molecule to be effective at decreasing the deleterious effects of Alzheimer's Disease, it is desirable for the small molecule to increase LDLR expression in mammalian cells. Previously, reports published the critical roles of ApoE receptor, low density lipoprotein receptor (LDLR), in regulating ApoE clearance and Aβ levels in the brain (Kim J, et al. (2009)). Overexpression of LDLR in the brain dramatically inhibits amyloid formation by decreasing ApoE level and increasing Aβ clearance. These beneficial effects are seen with as little as just two-fold over-expression of LDLR. Therefore, increasing LDLR levels may represent a novel Alzheimer's Disease treatment strategy. Unlike other ApoE receptors, LDLR has an advantage of not affecting the trafficking and processing of the amyloid precursor protein (APP).

Experiments were set up to test whether the claimed compounds increase LDLR expression in cortical astrocyte cells. The experiments involved treating mouse cortical astrocyte cells (E3 astrocyte cells) with the claimed compounds at 10 μM concentration for an incubation time of 24 hrs. DMSO solvent was used as a negative control, because the compounds were dissolved in DMSO when applied to the cells.

Figure 6:
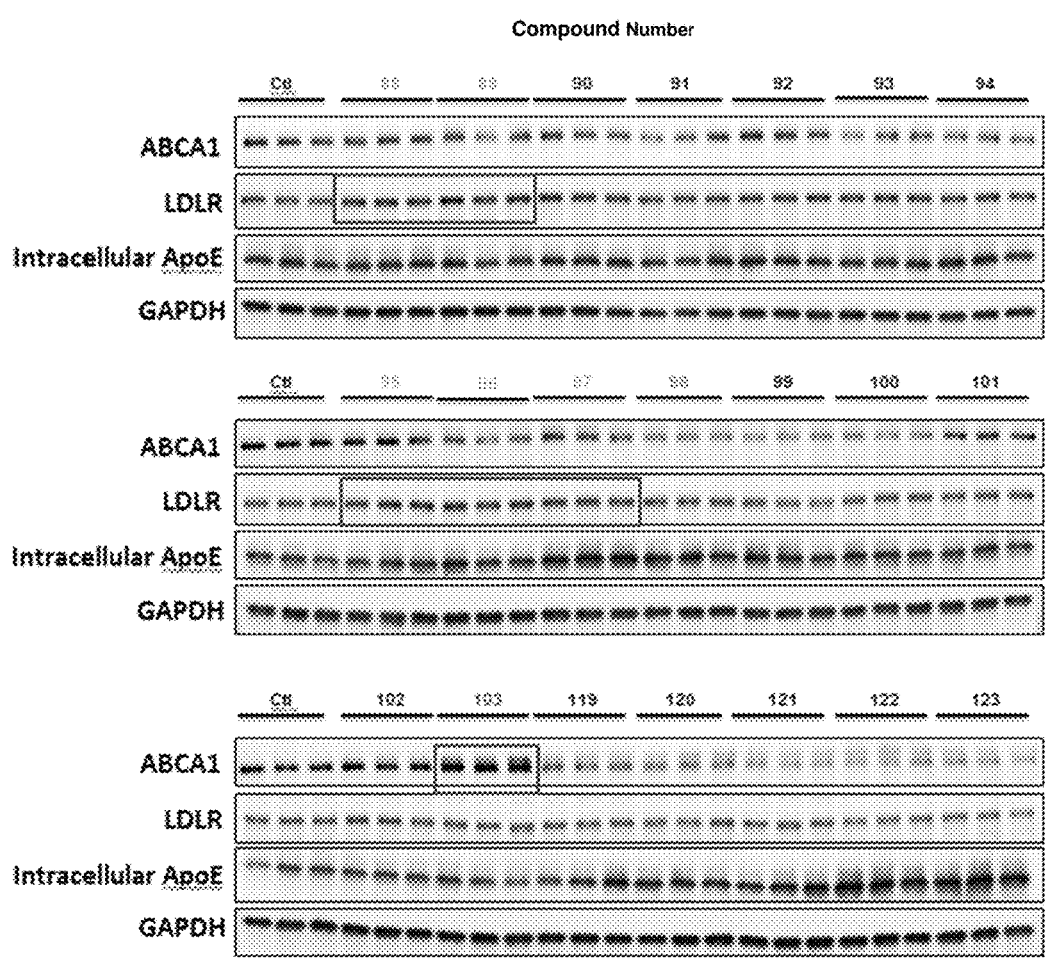
FIG. 6 shows a series of Western blot gel images depicting the effects of the identified compounds on the indicated protein levels in mouse cortical E3 astrocyte cells.
Figure 7:
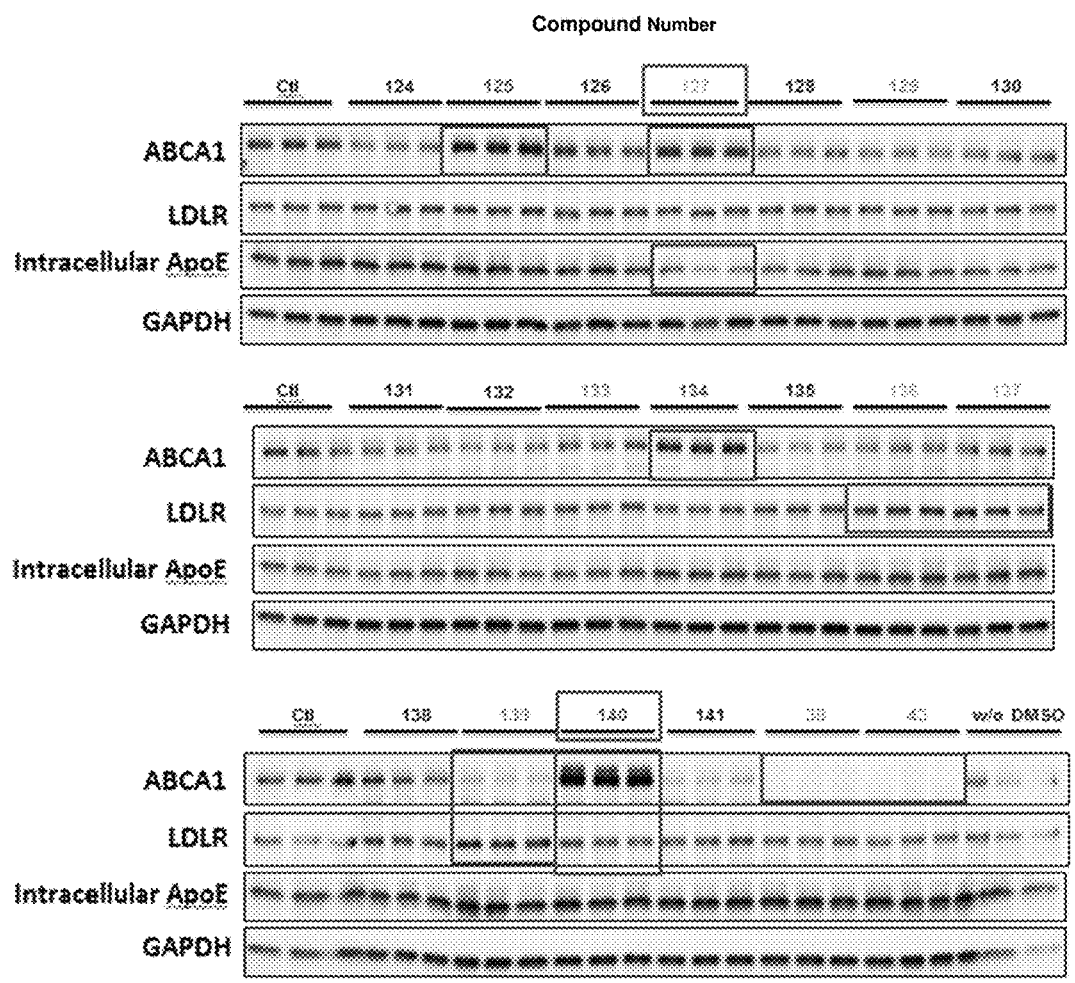
FIG. 7 shows a series of Western blot gel images depicting the effects of the identified compounds on the indicated protein levels in mouse cortical E3 astrocyte cells.

Western blot protocol and analysis was used to determine the LDLR levels in the E3 astrocyte cells. The western blot, otherwise known as a protein immunoblot, is a widely used analytical technique used to detect specific proteins in a cell culture or tissue sample. It uses gel electrophoresis to separate proteins by 3-D structure or denatured proteins by the length of the polypeptide. The proteins are then transferred to a membrane (typically nitrocellulose or PVDF), where they are stained with antibodies specific to the target protein. An image of the gel shows the presence of the stained antibodies attached to target proteins. FIGS. 6 and 7 show gel images showing the effects the claimed compounds have on the target proteins. The protein bands show the presence and amount of each target protein present in the media from treated cells (compound numbers shown in the column headers).

In this case, after the 24-hour culture period, the treated cell media from cells treated with each respective compound were run by electrophoresis on polyacrylamide gel containing sodium dodecyl sulfate (SDS). The proteins from the SDS-PAGE process were then transferred to a nitrocellulose gel and stained.

FIGS. 6 and 7 show the presence of the following proteins in mouse E3 astrocyte cells: AbcA1, LDLR, ApoE3, and GAPDH. The GAPDH protein serves as the loading control protein for the western blot analysis. For each of the claimed compounds, FIGS. 6 and 7 show three samples run to determine the presence and amount of each indicated protein. The three samples for each treatment compound are indicated by the line under the compound number—the line stretches across three columns of protein bands.

As shown in FIGS. 6 and 7, some of the claimed compounds increase LDLR expression in the E3 astrocyte cells compared to the DMSO control sample. Compound nos. 88, 89, 95, 96, 97, 136, 137, 139 and 140 all increased the amount of LDLR protein in the treated cell media compared to the control. Specifically, 88, 89, 95, 96, 97, 136, 137, 139 and 140 all increased LDLR expression in mammalian cortical astrocyte cells compared to the control DMSO.

iii. Claimed Compounds Increase AbcA1 Expression.

As described below, and as shown in FIGS. 6 and 7, the compounds from Table 1 were screened for their effect on AbcA1. AbcA1 protein plays a key role in regulating cholesterol in biological systems and therefore affects amyloid beta plaque formation. The goal of the biological screen (results shown in FIGS. 6 and 7) was to find compounds that prevent amyloid beta (Aβ) plaque formation, one of the deleterious causes of Alzheimer's Disease.

For a small molecule to be effective at decreasing the deleterious effects of Alzheimer's Disease, it is desirable for the small molecule to increase AbcA1 expression in mammalian cells. Previously, the critical roles of AbcA1 in regulating ApoE lipidation and Aβ levels in the brain were reported (Koldamova R, et al. *Neurobiol Dis* (2014) 72:13-21; Liu Y and Tang C. *Biochem Biophys Acta* (2012) 1821:522-529; Wahrle, S. E., et al. *J. Clin. Invest.* (2008) 118:671-682.). Overexpression of AbcA1 decreases Aβ levels by inhibiting its production and facilitating its clearance in vitro, and increasing AbcA1 expression decreases Aβ deposition in the brain of Alzheimer's disease mouse models, whereas deletion of AbcA1 gene exacerbates Aβ deposition in the brain. Therefore induction of AbcA1 is expected to prevent or attenuate Alzheimer's Disease phenotypes by decreasing the toxic Aβ levels.

As shown in FIGS. 6 and 7, some of the claimed compounds increase AbcA1 expression in the E3 astrocyte cells compared to the DMSO control sample. Compound nos. 103, 125, 127, 134, and 140 all increased the amount of LDLR protein in the treated cell media compared to the control. Specifically, 88, 89, 95, 96, 97, 136, 137, 139 and 140 all increased LDLR expression in mammalian cortical astrocyte cells compared to the control DMSO. As shown in FIG. 7, triarylmethyl amine compound nos. 38 and 39 significantly decrease or inhibit AbcA1 expression in the E3 astrocyte cells. Also, as shown in FIG. 7, compound no. 139 decreases AbcA1 expression significantly while increasing LDLR expression in the E3 astrocyte cells compared to the DMSO control sample. Continuing with FIG. 7, compound no. 140 increases AbcA1 expression significantly while also increasing LDLR expression slightly in the E3 astrocyte cells compared to the DMSO control sample.

iv. Claimed Compounds Affect Intracellular ApoE Levels

Intracellular apoE levels as measured in FIGS. 6 and 7 are the amounts of apoE inside of cells. Intracellular pool of apoE represents the apoE synthesized and taken up by cells. ApoE inside of cells provide additional mechanistic insight that explains how apoE levels in the cell culture media (i.e. outside of cells, extracellular) was altered by the compounds. For example, if intracellular and extracellular apoE levels were decreased similarly, this finding suggests that the compound inhibited apoE expression. If intracellular apoE levels were not altered while extracellular apoE levels were decreased, these data suggest that the compound inhibited the secretion of apoE to cell culture media. Specifically, the intracellular apoE levels corresponded to the apoE3 levels.

As shown in FIGS. 6 and 7, compound no. 127 increases AbcA1 expression while decreasing intracellular apoE expression in the E3 astrocyte cells compared to the DMSO control sample. Compound no. 127 is a compound that should be investigated further as a treatment option for Alzheimer's Disease because it both increases AbcA1 expression while decreasing apoE expression in mammalian cells.

EXAMPLE NO. 5

Compounds Administered to Cortical Astrocyte Cells and Analyzed by SDS-PAGE and Western Blot to Determine Effects on LDLR Expression and AbcA1 Expression The E3 astrocyte cells ($1.6 \times 10^4$ cells/96-well plate) were grown for 1 day in RPMI, followed by a 24 hour equilibration in serum-free Opti-MEM (Life Technologies). Treatments were carried out in triplicate with 100 μM of fresh Opti-MEM containing 10 μM of compound or vehicle (0.1% DMSO) for 24 hours. Each well was treated with one of the compounds listed in Table, at 10 μM concentration. After the incubation time, the cellular media was collected as samples.

The collected samples were prepared for SDS-PAGE and western blot analysis by centrifuging and then extracting the protein by TCA-precipitation. The extracted protein was then resuspended in a Tris buffer.

After incubation and collection, the samples were run on a SDS-polyacrylamide gel (10% SDS). The SDS-polyacrylamide gel comprises the following:

| | |
|---|---|
| 4 mL 10% resolving gel mix (dH2O | 48 ml |
| 40% acrylamide mix | 25 ml |
| 1.5M Tris, pH 8.8 | 25 ml |
| 10% SDS | 1 ml) |
| 75 μL 2% APS (ammonium persulfate) | |
| 7.5 μL TEMED | |

Each sample was prepared to run on the SDS-polyacrylamide gel. About 20 μL of each sample was prepared to be run in the gel. The samples were prepared comprising the following:

| | |
|---|---|
| 10X SDS Gel Loading Buffer | 2 mL |
| 20% SDS | |
| 500 mM Tris, pH 7.6 | |
| 1% Bromophenol Blue | |
| 50% Glycerol | 4 mL |
| Protein sample | 12 μL |
| 1M DTT | 2 ml |

The SDS-PAGE process was run with SDS-PAGE running buffer (Tris base, glycine, and 10% SDS) at 150 V until the dye front reached the bottom of the gel.

For the western blot portion of the analysis, the separated protein bands in the gel are then transferred to a nitrocellulose membrane by methods well known in the art. Following the western blot transfer, the blot is rinsed several times with $dH_2O$ to remove the salts. After blocking unreacted sites on the nitrocellulose membrane, all protein bands are stained with 0.5% Ponceau S (0.5 g Ponceau S, 1 ml Glacial HAc, 99 ml dH2O) and the target protein antibody.

The antibodies used for staining AbcA1 were obtained from Novus (NB100-2068). The antibodies used for staining LDLR were obtained from MBL International (JM-3839). The antibodies used for staining intracellular apoE were obtained from Meridian Life Science (K74180B). The antibodies used for staining GAPDH were obtained from Santa Cruz (sc-25778).

The compounds of this invention are found to be potent inhibitors of apoE expression while increasing the expression of one of LDLR or AbcA1, or both LDLR and AbcA1. As such, this invention contemplates using the compounds of this invention (as listed in Table 1), to inhibit apoE expression in mammalian cells, either in vivo or in vitro, while increasing the expression of at least one of LDLR or AbcA1.

As shown in FIGS. 6 and 7, the compound nos. 88, 89, 95, 96, 97, 136 and 137 are shown in light gray, and these compounds all increase LDLR expression. As shown in FIGS. 6 and 7, the compound nos. 103, 125, 134 and 140 are shown in red, and these compounds all increase AbcA1 expression. As shown in FIGS. 6 and 7, the compound nos. 98, 129, 133, 139, 38 and 39 are shown in light blue, and these compounds all decrease AbcA1 expression. As shown in FIGS. 6 and 7, the compound no. 127 is shown in green, and this compound increases AbcA1 expression while decreasing intracellular apoE levels.

A number of embodiments of the invention have been described. Nevertheless, it will be understood that various modifications may be made without departing from the spirit and scope of the invention. Accordingly, other embodiments are within the scope of the present invention.

We claim:

1. A method for decreasing expression of apolipoprotein E and increasing expression of at least one of either LDL-receptor protein or AbcA1 protein comprising:
    selecting mammalian cells expressing apolipoprotein E and at least one of either LDL-receptor protein or AbcA1 protein;
    contacting said mammalian cells with an effective amount of a compound having formula (I) in an amount sufficient to decrease expression of said apolipoprotein E and increase expression of at least one of said LDL-receptor protein or said AbcA1 protein in said mammalian cells:

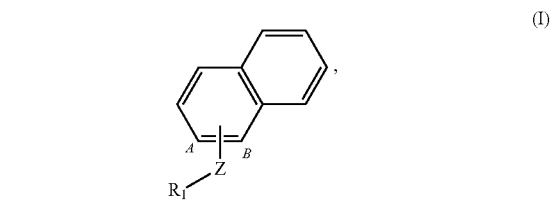

wherein Z may be at either position A or position B and may be selected from the group consisting of: $CH_2$, CO, or $SO_2$, and wherein $R_1$ may be selected from the group consisting of:

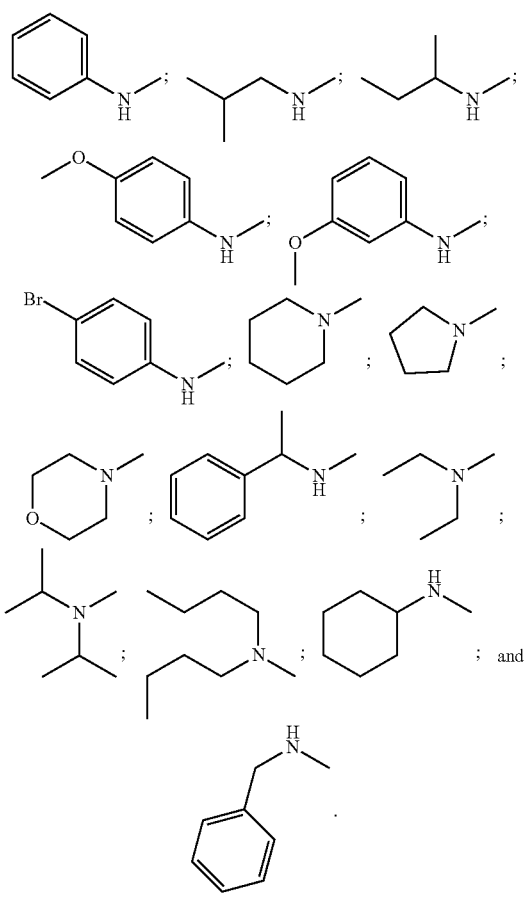

2. A method according to claim 1, wherein said selecting step selects for mammalian cells expressing apolipoprotein E, LDL-receptor protein, and AbcA1 protein, and wherein said method decreases apolipoprotein E and increases expression of both said LDL-receptor protein and said AbcA1 protein.

3. A method according to claim 1, wherein said effective amount is 10 μM.

4. A method according to claim 1, wherein said method decreases expression of apolipoprotein E and increases expression of AbcA1, wherein said Z is located at position A and is $SO_2$, and wherein said $R_1$ is

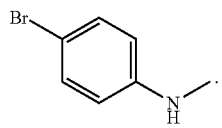

5. A method according to claim 1, wherein said method decreases expression of apolipoprotein E and increases expression of LDL-receptor protein, wherein said Z is located at position A and is $CH_2$, and wherein said $R_1$ is

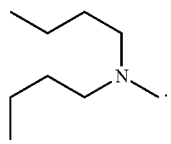

6. A method according to claim 1, wherein said method decreases expression of apolipoprotein E and increases expression of AbcA1, wherein said Z is located at position A and is $CH_2$, and wherein said $R_1$ is

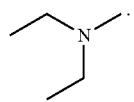

* * * * *